(12) United States Patent
Large

(10) Patent No.: US 7,481,779 B2
(45) Date of Patent: Jan. 27, 2009

(54) METHOD OF MANAGING AND PREVENTING THE ONSET OF COMPUTER AND SEDENTARY WORK RELATED FATIGUE

(76) Inventor: William Thomas Large, 140 Old Country Rd., Ste. 205, Nineola, NY (US) 11501

( * ) Notice: Subject to any disclaimer, the term of this patent is extended or adjusted under 35 U.S.C. 154(b) by 187 days.

(21) Appl. No.: 11/186,178

(22) Filed: Jul. 21, 2005

(65) Prior Publication Data
US 2007/0017531 A1   Jan. 25, 2007

(51) Int. Cl.
*A61B 5/117* (2006.01)
*A61B 5/103* (2006.01)
*A61B 19/00* (2006.01)

(52) U.S. Cl. ................... 600/594; 128/898

(58) Field of Classification Search ............ 600/587, 600/594, 595, 300, 26–28; 379/93.24, 90.01; 705/1; 455/412.1; 128/898, 905, 907; 273/292; 607/62, 46, 48; 601/15; 297/218.1; 472/137; 250/324, 423 F, 423 R; 361/230, 231; 345/168, 345/167; 248/181.1, 288.31, 918; 341/22; 400/486, 704; 702/176; 706/926; 434/236
See application file for complete search history.

(56) References Cited

U.S. PATENT DOCUMENTS

| | | | |
|---|---|---|---|
| 3,873,835 A | 3/1975 | Ignatjev | |
| 5,304,112 A | 4/1994 | Mrklas | |
| 5,305,238 A | 4/1994 | Starr, III | |
| 5,311,210 A | 5/1994 | O'Brien | |
| 6,118,856 A * | 9/2000 | Paarsmarkt et al. | 379/93.24 |
| 6,554,781 B1 * | 4/2003 | Carter et al. | 600/594 |
| 6,673,027 B2 * | 1/2004 | Fischer | 600/595 |
| 2002/0133367 A1 * | 9/2002 | Miyazaki et al. | 705/1 |
| 2004/0077424 A1 | 4/2004 | Murphy | |
| 2006/0108739 A1 | 5/2006 | Lutz | |

* cited by examiner

*Primary Examiner*—Max Hindenburg
*Assistant Examiner*—Brian Szmal
(74) *Attorney, Agent, or Firm*—Jennifer Meredith, Esq.; Meredith & Keyhani, PLLC

(57) ABSTRACT

A microprocessor implemented method of managing and preventing the onset of computer related fatigue, the method comprising the steps of: providing a user; determining when the user begins fatigue inducing activities to provide a start time; requiring an anti-fatigue break for a predetermined anti-fatigue time period after the start time; disengaging the user through a staged process sequence; and preventing the user from being able to perform the fatigue inducing activities for a predetermined anti-fatigue time period.

2 Claims, 2 Drawing Sheets

Figure 1:
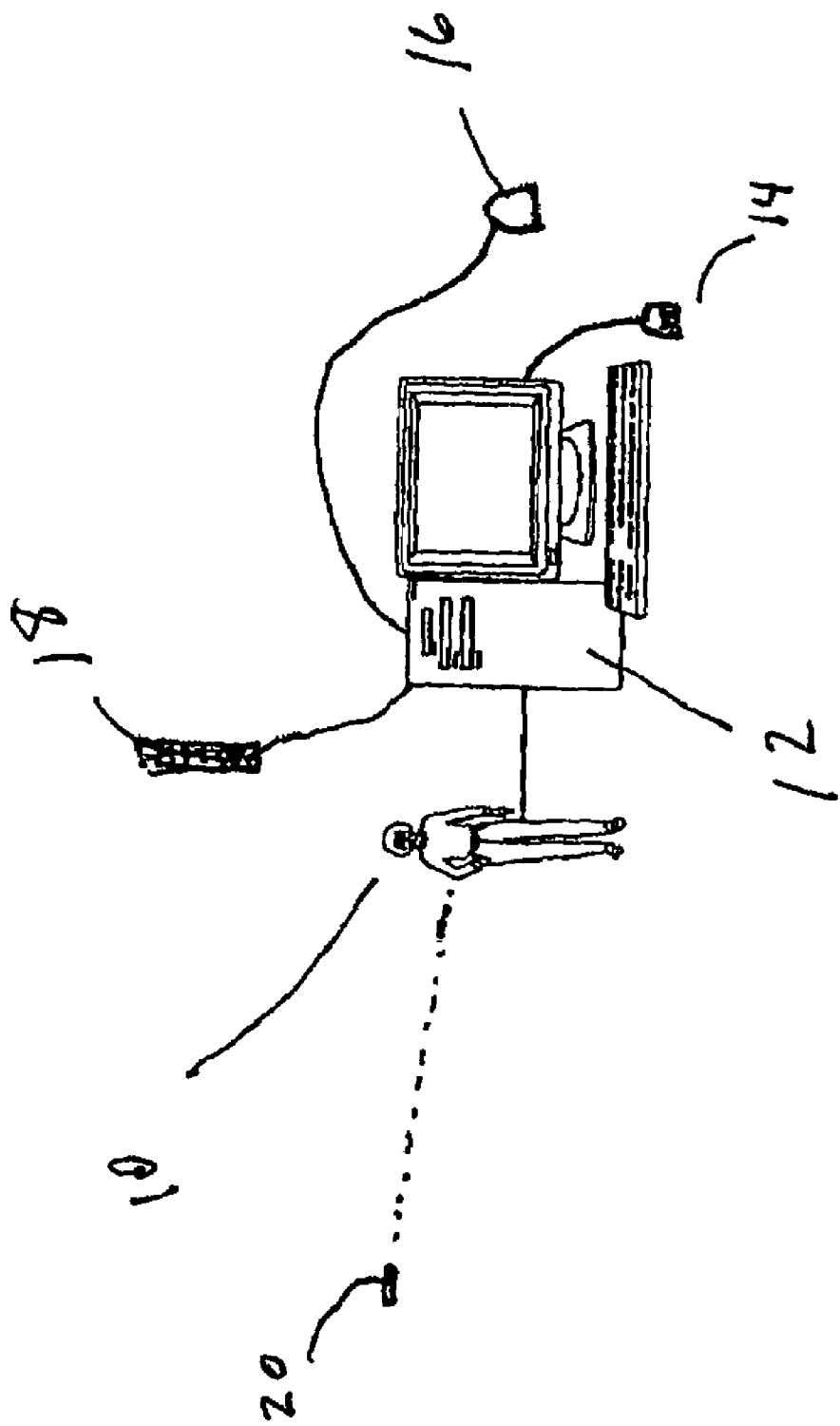

METHOD OF MANAGING AND PREVENTING THE ONSET OF COMPUTER AND SEDENTARY WORK RELATED FATIGUE

The present invention relates generally to methods and systems for managing and preventing the onset of computer and sedentary work related fatigue.

Sedentary work has for many years been regarded as "light work" and references such as "sat at a desk" have often represented the perception that little effort is anticipated in the execution of such work. That view is now being reexamined in the light of a growing body of evidence that indicates such work creates fatigue due to normal yet undetectable physiological changes that are causing injury and impairment, to computer users particularly. Direct evidence as to the exact cause and consequence of injury has been hindered due to what are slowly developing chronic conditions resulting in diffuse, non-specific in their medical nature and so designated, "syndromes".

Repetition was once considered as the most likely causal agent of impairment and so the expression "Repetitive Strain Injury" has generally been coined in relation to computer user's injuries, but not limited to it. However the appearance of so called "ergonomic keyboards" in the later part of the 1990's appears to have done little to stem the tide of injury to the extent that the European Union issued a press release on Nov. 12, 2004 and entitled "Commission asks workers and employers what action should be taken to combat musculoskeletal disorders". In the release they cited "The European Commission is seeking the views of workers' and employers' representatives on how best to tackle the growing problem of musculoskeletal disorders (MSD). These ailments, which include back pain and repetitive strain injury, are the biggest health and safety problem facing European workers today. Studies show that they affect over 40 million workers in all sectors across the EU and account for 40 to 50 percent of all work-related ill-health. They are costing employers across the EU billions of euros. The problem is eroding Europe's competitiveness and leading to losses of 0.5 to 2 percent of GNP each year."

In relation to a statement correlating to computer workstation design stated: "The highest increases are being seen amongst professionals (up from 18 percent to 24 percent) and technicians (up from 23 percent to 31 percent)". Carpal Tunnel Syndrome (CTS) is another RSI related condition. A 2004 National Institute of Occupational Safety and Health (NIOSH) report states, in regard to Californian statistics, the 'Number of CTS cases in California by type of job activity, 1998-2000: Among the cases sampled, computing (data entry) activities consistently accounted for nearly half of all CTS cases in California for each of the 3 years during 1998-2000'."

Recent hypothesis focus on the type of posture and not the work performed leading to the development of products that require less static posture like grip, applied to manipulate market standard computer mouse, wherein muscles are tensed and held tense for extended periods and so fatigue sets in. The physiology of this type of fatigue is associated with lactic acid production and is the most damaging. The other, typical, working posture is that of dynamic posture, such as typing, which involves short-term cyclical contraction and relaxation of muscles. The physiology of this fatigue is substrate or energy exhaustion and is quickly recovered from, but nonetheless wearing and when used in conjunction with static postures, such as gripping and clicking computer mice, it increases the consumption of substrate and adds to the production of lactic acid. So while it is unlikely to cause frequent and extended excursions into regional/cellular fatigue (each cell is an "independent engine" so will respond individually to local blood supply and the resource that makes available) by itself it creates fatigue dependent upon the rate of cleansing and replenishment by the blood supply to those cells in those muscles involved.

Research using micro dialysis techniques reported in 2004 concluded in a revelation that muscle metabolism was observed that is not detected systemically (L. Roesendal et al). It disclosed for the first time the possibility also that muscle fiber activation occurred "inhomogenously" during low-force contractions creating circulatory disconnected zones that explained the possibility of localized intramuscular anaerobic conditions. This adds further to the unreliability of perception and detection so responses to low force sedentary work metabolic risk.

The rate of fatigue development is dependent upon blood flow to the region of the body that is active when the rest of the body is under a sedentary condition. When we are resting the body does not anticipate muscles in the hand to be "active" nor that we might sit for many hours working small hand muscles extensively while larger muscles are inactive. So why do we not detect or perceive fatigue that Sejersted & Vollestead suggested in 1993 was a possible precursor to muscle pain. One new answer is Cognitive Distraction, the suppression of the cognitive recognition of fatigue requiring the need to manage work fatigue empirically by the solution that is defined herein.

Fatigue has a twofold circumstance: The local physiological consumption of resource such as oxygen, glucose and other nutrients in excess of their replenishment and the inadequate removal of toxic metabolic byproducts like carbon dioxide, uric acid and lactic acid (the latter as a result of low aerobic operating conditions). The former generally creates feelings of weakness and the latter invokes systemic feelings of fatigue such as aches and pain.

Research into Pain Management, such as in recurrent Migraine bouts, teaches us that people who suffer acute or chromic pain are able to suppress their perception of pain to some extent by engaging in a cognitive task. The use of video games for instance, that might be considered by many is "headache causing", have been found to help suppress pain perception during migraine attacks and are recommended for the same.

Research work into this has elucidated a neurological explanation as to this (Imaging how attention modulates pain in humans using MRI: Bantick et al: Brain (2005), 15, 310-319), which is akin to the electronic principle of the diode. That is that circuits overlap and interact and so pain perception intensity can be reduced when cognitive circuits are stimulated, akin to a load being placed across the base emitter of a diode reducing the output voltage to another and separate circuit.

Analogously this can be likened to the volume circuit of a fire siren being attenuated, so reducing the audible output even though the sensor signal that triggered the event is not attenuated. This comparison does not presuppose any new discovery that may be made that explains the mechanism further but provides for a working and practical model as to why "low order pain signals" such as aches that are known to occur in fatigue states can be suppressed. It can therefore likely explain the prevalence and occurrence of syndromes associated with RSI's that can all, theoretically, be extrapolated from known physiological circumstance and thereby explained by fatigue states not being noticed so not managed resulting in chronic injuries and impairments that develop slowly over a period of time. The issue is that if you do not ache then you are far less likely to go on to injure. This then allows for a novel invention herein described that is applicable to the assessment and empirical management of work related fatigue where a requirement for cognition and attention to the work is a primary component of the task function.

Prior art cited states the therapeutic benefits of an amalgam of techniques and prior art itself does not lay claim to novelty of the techniques but either the objective or the conformation of how such established practice might be constructed.

Lasmon and Krass teach of the therapeutic benefits of their novelty in terms of diagnosis or treatment of preexisting clinical conditions. Douglas et al, supports this view in its discussion and then seeks to protect its iteration of the form of the amalgam while laying no claim to novelty within the use of such techniques in of itself. Hirsch teaches of the impact of different olfactory stimulants and seeks to enhance learning skills thereby and so engage and enhance cognitive work focus and not to detract from it as in this case.

Prior art anticipates the need for work breaks but without such orthogonal knowledge or understanding and explanation of the consequences of work in terms of cognitive distraction and its impact upon the ability to anticipate, perceive or explain fatigue states and thereby orchestra an effective process to combat it. Consequently there is a focus and undue assumption upon a quantum of work as typically measured as elapsed time and in one example of orthogonal art, relates "Strain" directly to time. Such programs are often called "Work Break Timers" which will call a break based upon keystrokes or mouse clicks or chronological periods of activity or on a designated time period in of itself.

Such breaks are, cognitively speaking, an interruption and will typically impinge upon the psyche of the individual and so can be counterproductive in terms of the "stress" they claim to remediate. Often they will offer invasive displays announcing a forthcoming break that will typically heighten physiological tension, which contributes to fatigue, as the user is already in a task orientated mode and under a cognitive load so the impending break notification adds to the pressure of such a load. Such breaks offer a period away from work activity but without detracting the user from the work or cognitive load sufficiently to de-couple the user from the work to which focus and cognitive attention remains attached. The impact of this is that the mechanism such prior and orthogonal art imparts as to break activities is less or ineffectual insofar that the user fails to make a transition out of work mode and into "break mode" and therefore frequently fail to take the break or effectively employ the mechanism advocated during the break.

This is due to several factors: firstly that there is no perceived cognitive reward as the break itself is perceived as a work distraction and therefore is not prioritized as a necessary component to the attainment of the work. This is an important and necessary element as the motivation for the use of such mechanisms is key to a successful outcome. Those who are injured and impaired already will have a higher motivational threshold for taking breaks, whereas the object and benefit of this invention, we respectfully suggest, is to be a tool that is more easily assimilated, understood and used by those without injury or impairment as well as those with so that the likelihood and impact of injury and impairment is diminished by the utilization of the invention herein disclosed.

Secondly the user is not transitioned into a "break mode" so assimilates and cognitively enters into the break due to an overriding attention to the work, "break distraction", which can also be argued as a subcomponent of the first reason cited. Thirdly the break activities themselves are not cognitively engaging, enjoyable or easily assimilated under the circumstance by which they required to be enacted, typically in the workplace environment. So as standard operating procedures they are commonly unsustainable as routine activities and so the desired outcome that the purveyors of such "work break" products suggest is not achieved. This is felt to be especially true of the "exercise break timers". Such products will typically chronologically call up a break and display images of suggested movements as exercises to be performed at the location of the operator. The psychology of the work and worker is paramount to a successful outcome and so benefits of these products, based upon the personal experience as a non impaired user researching Cognitive De-Coupling and a small survey of others of a like that the contortions so prescribed within such break activities are not sufficiently cognitively motivating so as to make them desirable or sustainable public behavior.

The delivery mechanisms referred thus far typically relates to computer mediated breaks and while this is one mechanism of delivery of this invention it is not anticipated as the only mechanism of delivery, as the process and mechanism herein described can relate to the use of other such media as in paper, video, digital, verbal and any other media innovation that time and technology can be anticipated to create as an alternative media environment to which this invention would also pertain.

Another important component to the principal of Cognitive De-Coupling therefore is a process of Cognitive Reassignment. In order to reassign cognition to an alternative priority it must therefore by made a priority and be assimilated into a standard working practice that meets the criteria of understanding, need, enactment and achievement in a manner that is cognoscente.

For instance any new learning must be assimilated by the autonomic system for it to become a work habit. Once a work habit then the benefits of the practices herein described and learnt are therefore sustain-ably gained. Therefore the manner and mechanism of the Cognitive De-Coupling process must meet basic human criteria for sustainable behavior insofar that it is understood and prioritized by all users and not just by those who are impaired. The mechanism must not conflict with sociological, medical or psychological criteria that may be tested by each user in assigning a Cognitive Priority to performing the break. Therefore the mechanism of Fatigue Breaks employing Cognitive De-Coupling and re-assignment are designed specifically for and is novel to the work break field.

SUMMARY OF THE INVENTION

The present invention relates generally to methods for managing and preventing the onset of computer and sedentary work related fatigue.

According to one aspect of the present invention, a microprocessor implemented method of managing and preventing the onset of computer related fatigue is disclosed the method comprising the steps of: providing a user; determining when said user begins fatigue inducing activities to provide a start time; requiring an anti-fatigue break for a predetermined anti-fatigue time period after said start time; disengaging said user through a staged process sequence; preventing said user from being able to perform said fatigue inducing activities for a predetermined anti-fatigue time period.

According to another aspect of the present invention, a microprocessor implemented method of managing and preventing the onset of computer related fatigue is disclosed, the method comprising the steps of: providing a user; determining the posture of the user; providing a predetermined anti-fatigue time period according to said posture; determining when said user begins fatigue inducing activities to provide a start time; requiring an anti-fatigue break for said predetermined anti-fatigue time period after said start time; disengaging said user through a three staged process sequence of stage one, stage two and stage three, wherein said stage one is "Cognitive De-coupling" from the work task and is followed by said stage two, wherein stage two consisting of cognitive assignment to a counter fatigue activity and stage three consisting of engaging in cognitive relief for a period of relaxation that allows for the counter fatigue measures to maximize their impact; preventing said user from being able to perform said fatigue inducing activities for a predetermined anti-fatigue time period; providing aromatherapy during said predetermined anti-fatigue time period; and (step 132) providing at least one non task related stimulus during said predetermined anti-fatigue time period.

This summary is not to be taken in a limiting sense, but is made merely for the purpose of illustrating the general principles of the invention, since the scope of the invention is best defined by the appended claims.

BRIEF DECRIPTION OF DRAWINGS

Figure 2:
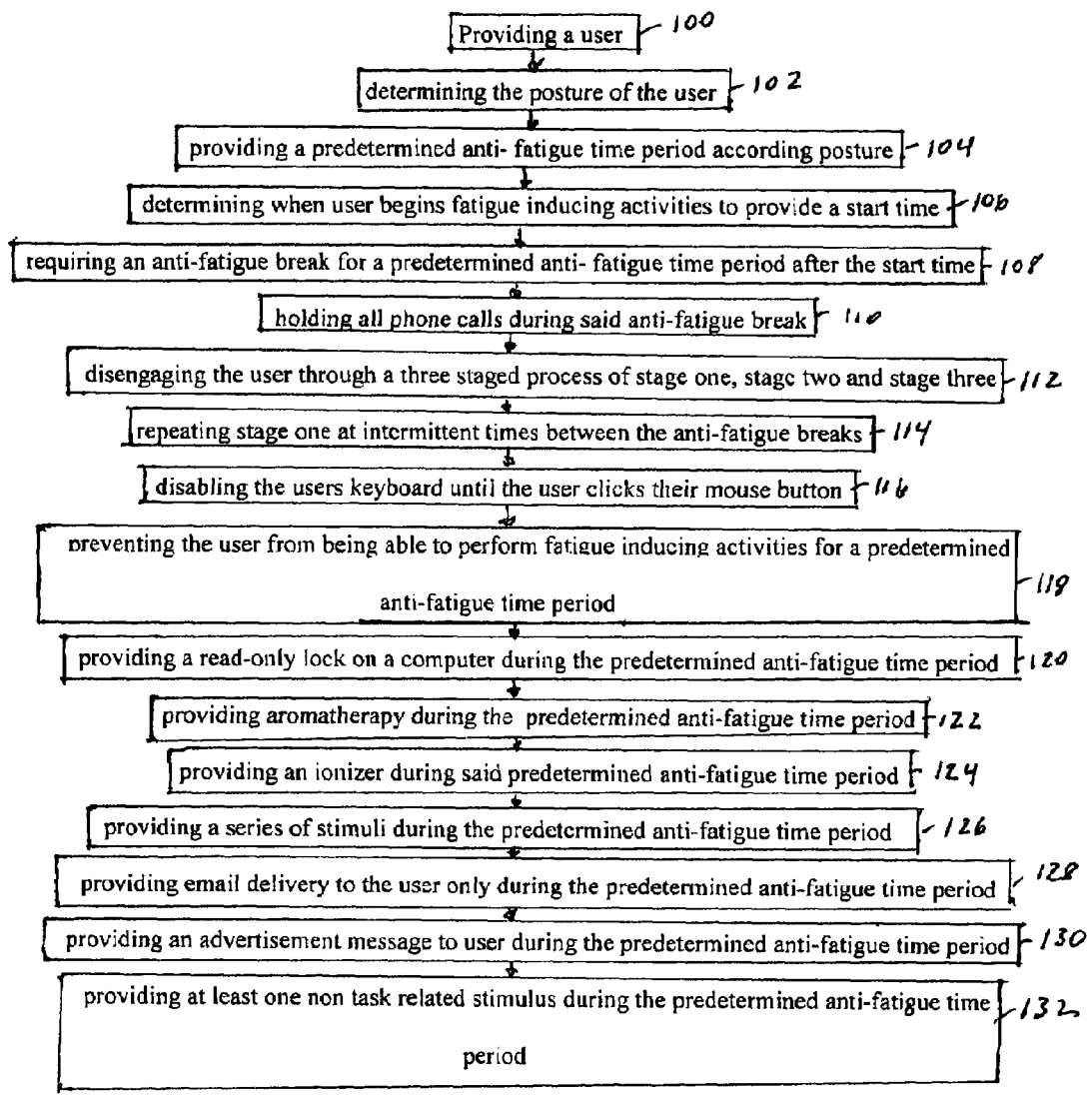

FIG. 1 depicts a system according to the present invention; and
FIG. 2 depicts a method according to the present invention.

DETAILED DESCRIPTION OF THE INVENTION

A microprocessor implemented method of managing and preventing the onset of computer related fatigue, the method comprising the steps of: (100) providing a user (10); (106) determining when the user (10) begins fatigue inducing activities to provide a start time; (108) requiring an anti-fatigue break for a predetermined anti-fatigue time period after the start time; (112) disengaging the user (10) through a staged process sequence; (118) preventing the user (10) from being able to perform the fatigue inducing activities for a predetermined anti-fatigue time period. It is important that the invention be understood to be applicable to a wide range of applications, as the invention only need be microprocessor implemented. This is to say that the invention may be utilized on a computer (12), a hand held device, pda, telephone, blackberry or other similar device. It is envisioned to be applicable to computer (12) work as well as any sedentary work.

The predetermined anti-fatigue time period may be set according to the fatigue state of the activity being performed by the user (10). An important and heretofore not provided aspect of the present invention is varying to predetermined anti-fatigue time period according to the type of activity being performed. The duration spent in "kinds of activity" and activity alone does not prescribe the risk of damage, especially when experts define different risk and consequence for different types of activity. The risk of consequence is also intrinsic to the normal operation of the computer (12) input system when the system is defined and understood.

In terms of a normal process of damage, all "activity" has an impact upon the cell collectives such as muscle, soft tissue etc, which function under the principal of "united we stand and divide we fall". So if one cell gets into "trouble" then it is on its own and makes it own independent decision as to what to do next and there are two types of trouble for a cell. Running out of substrate (oxygen, energy, etc) after which it enters a back up metabolism, anaerobic or lactic acid metabolism, which if unchecked leads to a build up of acid.

So a structure and process or remedy is defined that recognizes that activity has impact as a result of the posture it prescribes verses the duration spent within it and that user activity is not simply injurious or accidental. Ache Fatigue: is the first stage whereby the cells are reaching their aerobic substrate exhaustion point and if a break from the posture that invokes it is taken at that time then full recovery is likely with little harm. Pain Fatigue: is when we work beyond ache fatigue, which we are designed to do as a back up though it causes a build up of anaerobic byproducts, a.k.a. toxins. Now we have tolerance for this, but how much is impossible to say as it is entirely personal and will vary with your mood, metabolism and last meal to a certain extent and is therefore a function of duration in a "type of posture" and not linearly correlated with activity.

Research suggests that if you manage fatigue ache onset so as not to spend too long a time in the Pain Fatigue zone then you are less likely to damage. Ache, as pain, is a "lower order" pain signal and migraine research teaches of Cognitive Distraction, if you are busy doing "thinking work", which is involved in only some activity, preoccupation with it may mean that you might not notice and continue on and dwell under Pain Fatigue conditions. Damage is always as a result of the posture in which the work activity is performed vectored by the duration that the posture is maintained for. There are typically three kinds of posture in relation to individual muscular activity: functional neutral; dynamic posture; and static posture. Functional neutral is allowing muscles, typically the small muscles at limb extremities that are most likely at risk, to remain predominantly idol and so deploys larger muscles to do the work; the larger muscles being more resilient to the load that small muscles are asked to perform due to relative scale and they are employed under a Dynamic Posture mechanism, which is a medium duration risk posture. This allows for the performance of tasks, functioning, while most at risk muscles are in neutral. If you can organize Functional Neutral posture then you can typically extend the other vector, duration of work. Dynamic Posture is the cyclical use of muscle so contracting and relaxing them. Each time you do you are squeezing the blood out on contraction and always drawing in heart side, so fresh, blood on relaxation. Used on its own it is a lesser issue if the time vector is managed but if you are using Static Posture at the same time, as in the input activity of gripping and clicking a mouse (14), Dynamic Posture is further strain on top of "static stress". It is a "mid range" medium duration risk posture in our work duration vector. Static Posture: The highest damage risk, as every muscle cell under contraction is effectively cut off from the blood supply for the duration of the contraction. So you have to relax them to refresh them and the longer they are under contraction (and the degree of contraction so how metabolically active they are) the longer they need to re-equilibrate and move toxins out. This is our highest duration risk posture.

Accordingly, a sensor (20) may detect the posture of the user (10) (functional neutral, dynamic posture and static posture) (step 102). Upon (102) determining the posture of the user (10), predetermined anti-fatigue time period may be adjusted according to the posture (step 104). For example, if the sensor (20) determines that the user (10) is in a functional neutral position, the predetermined anti-fatigue period may be extended. If the sensor (20) detects that the user (10) is in a static posture, the predetermined anti-fatigue period may be shortened.

The step of (118) preventing the user (10) from being able to perform fatigue inducing activities may comprised of the step of blocking the user (10) from using their computer (12). Alternatively, the step of preventing the user (10) from being able to perform fatigue inducing activities is comprised of the step of cognitively and voluntarily impeding the user (10) from using their computer (12). The steps of blocking the user (10) and cognitively and voluntarily impeding the user (10) may be set according to an administrator. During the predetermined anti-fatigue time period, there may be the step (110) holding all phone calls during the anti-fatigue time period.

The step (112) of disengaging the user (10) may be a three stage process consisting of stage one, stage two and stage three. Stage one may be "Cognitive De-coupling" from the work task. This is to say the user (10) is diverted from work. Such a diversion may be underpinned by use of a Soft Disable function in which input functionality is impeded but easily and quickly reactivated by the use of a signal generated as if by a mouse (14) button. This may be according to step (116) disabling the users keyboard until the user (10) clicks their mouse (14). If the signal is not given then the input function is automatically re-enabled upon completion of stage one unless conditions, relating to stage two or three, prevail that mean otherwise. They may be reminded to breathe in deeply, Deep breathing elevates respiration that are learnt to be associated with a self inspection program to raise awareness and attention to, and so scan, the body for aches. Stage one may be followed by stage two. Stage two may consist of cognitive assignment to a counter fatigue activity. This is where the user (10) focuses on themselves (and not on their computer work) by concentration and attention to muscles which releases tension from them. Stage three may consist of engaging in cognitive relief for a period of relaxation that allows for the counter fatigue measures to maximize their impact. This may be defined as a period of time with muscles relaxed so to provide more effective perfusion and an elevated blood oxygen level to re-equilibrating fatigue tissue more quickly and effectively as well as purging fatigue stress related toxins. Stage one may be repeated at intermittent times between the anti-fatigue breaks (step 114).

While it may seem that exercise during break would reduce fatigue, the present invention does not promote exercise during the anti-fatigue break. Exercise actually puts muscles under more effort but increases respiration, so aids circulation and replenishment. Deep breathing has the same physiological effect without further using the muscles that are tensed. Progressive visualization relaxes the muscles that relieves the tension and promotes blood flow. For example, the screen might state: Relax (hands in the lap) and stare at your hands for a minute and think of them as warm and bright pink. If you have been on the computer (12) for a while you will likely feel them throb, which is quite normal, or become aware of ache, which is not. It will only take seconds.

The method may further comprise the step of: (122) providing aromatherapy during the predetermined anti-fatigue time period. The step (122) of providing aromatherapy may be through an air freshener (16) in communication with the computer (12). The aromatherapy may also be selected according to an image displayed during the anti-fatigue break. For example, the image displayed may be a Yule tide log and the aroma may be the smell of a wood fire and the sound of a fire crackling. Another example may be a picture of roses with the scent of roses. It is also provided that an ionizer (18) may be provided during the predetermined anti-fatigue time period (step 124).

During the predetermined anti-fatigue period there may the step of providing at least one non task related stimulus. The stimulus may be heat, vibration, blown air, low voltage electricity and/or acupuncture. There may also be an auditory stimuli provided during the predetermined anti-fatigue time period. The auditory stimuli may be selected from the group consisting of natural sounds, electronic sounds, origination sounds, music, oration, an online book, text to speech reading. There may also be at least one visual stimuli during the predetermined anti-fatigue time period. According to the present invention, a series of stimuli may be provided during the predetermined anti-fatigue time period (step 126). The stimuli may be selected from the group consisting sensory, visual, olfactory and auditory stimuli. The series of stimuli may also be user (10) specific.

It is envisioned that during the predetermined anti-fatigue time period the computer (12) may be locked as a read-only lock (step 120). During this time emails may be delivered to the user (10). According to one embodiment, emails are provided only during the predetermined anti-fatigue time period (step 128). This accomplishes two goals: (1) minimized computer related fatigue; and (2) increased productivity. Computer related fatigue is minimized because the user (10) is only reading, not typing or clicking. Increases productivity may result because users are not constantly procrastinating with reading and sending emails. Also, all phone calls may be held or directed to voicemail during the predetermined anti-fatigue time period.

The method may comprise the step of providing a breathing reminder to the user (10) during the predetermined anti-fatigue time period. Also, during the predetermined anti-fatigue time period information may be provided including a warning, advice or instruction to the user (10). It is also provided that an advertisement message may be delivered to the user (10) during the predetermined anti-fatigue time period (step 130). The advertisement or promotion may be changed or updated by connection to a separate and remote source of such advertising material that would be interrogated from time to time.

This description is not to be taken in a limiting sense, but is made merely for the purpose of illustrating the general principles of the invention, since the scope of the invention is best defined by the appended claims.

I claim:

1. A microprocessor implemented method of managing and preventing the onset of computer and sedentary work related fatigue, said method comprising the steps of:

providing a computer and a computer user;

determining when said computer user begins fatigue inducing activities to provide a start time;

requiring an anti-fatigue break for a predetermined anti-fatigue time period after said start time;

disengaging said computer user through a staged process sequence;

preventing said computer user from being able to perform said fatigue inducing activities for a predetermined anti-fatigue time period; and providing a read-only lock on said computer during said predetermined anti-fatigue time period.

2. A microprocessor implemented method of managing and preventing the onset of computer and sedentary work related fatigue, said method comprising the steps of:

providing a computer and a computer user;

determining the posture of said computer user;

providing a predetermined anti-fatigue time period according to said posture;

determining when said computer user begins fatigue inducing activities to provide a start time;

requiring an anti-fatigue break for said predetermined anti-fatigue time period after said start time;

disengaging said computer user through a three staged process sequence of stage one, stage two and stage three, wherein said stage one is "Cognitive De-coupling" from the work task and is followed by said stage two, wherein stage two consisting of cognitive assignment to a counter fatigue activity and stage three consisting of engaging in cognitive relief for a period of relaxation that allows for the counter fatigue measures to maximize their impact;

preventing said computer user from being able to perform said fatigue inducing activities for a predetermined anti-fatigue time period; and providing aromatherapy during said predetermined anti-fatigue time period; and providing at least one non task related stimulus during said predetermined anti-fatigue time period; and providing a read-only lock on said computer during said predetermined anti-fatigue time period.

* * * * *